United States Patent
Knudsen et al.

(10) Patent No.: US 9,156,689 B2
(45) Date of Patent: Oct. 13, 2015

(54) PROCESS FOR REFORMING HYDROCARBONS

(75) Inventors: Bjerg Lari Knudsen, Kastrup (DK); Frahm Martin Jensen, Vallensbaek Strand (DK)

(73) Assignee: Haldor Topsoe A/S, Lyngby (DK)

( * ) Notice: Subject to any disclaimer, the term of this patent is extended or adjusted under 35 U.S.C. 154(b) by 504 days.

(21) Appl. No.: 13/542,292

(22) Filed: Jul. 5, 2012

(65) Prior Publication Data

US 2013/0345324 A1  Dec. 26, 2013

(30) Foreign Application Priority Data

Jun. 21, 2012 (EP) .................................... 12172986

(51) Int. Cl.
*C07C 1/02* (2006.01)
*C01C 1/04* (2006.01)
*C01B 3/38* (2006.01)

(52) U.S. Cl.
CPC ......... *C01B 3/382* (2013.01); *C01B 2203/0205* (2013.01); *C01B 2203/0233* (2013.01); *C01B 2203/0244* (2013.01); *C01B 2203/0255* (2013.01); *C01B 2203/0261* (2013.01); *C01B 2203/06* (2013.01); *C01B 2203/061* (2013.01); *C01B 2203/062* (2013.01); *C01B 2203/068* (2013.01); *C01B 2203/0844* (2013.01); *C01B 2203/0894* (2013.01); *C01B 2203/1235* (2013.01); *C01B 2203/141* (2013.01); *C01B 2203/142* (2013.01); *C01B 2203/143* (2013.01); *C01B 2203/1604* (2013.01)

(58) Field of Classification Search
CPC ............ C01B 3/382; C01B 2203/0233; C01B 2203/0244; C01B 2203/0255; C01B 2203/0261; C01B 2203/143; C01B 2203/062

USPC .......................................... 252/373; 423/359
See application file for complete search history.

(56) References Cited

U.S. PATENT DOCUMENTS

| | | | |
|---|---|---|---|
| 4,376,717 A | 3/1983 | Lagana' et al. | |
| 4,824,658 A | 4/1989 | Karafian et al. | |
| 6,296,679 B1 | 10/2001 | Kato | |
| 7,241,401 B2 | 7/2007 | Aasberg-Petersen et al. | |
| 7,314,891 B2 | 1/2008 | Abbott et al. | |
| 2009/0184293 A1 | 7/2009 | Han | |

FOREIGN PATENT DOCUMENTS

| | | |
|---|---|---|
| EP | 0 033 128 A1 | 8/1981 |
| EP | 0 334 540 A2 | 9/1989 |
| EP | 0 440 258 A2 | 8/1991 |
| EP | 0 504 471 A1 | 9/1992 |
| EP | 0 516 441 A1 | 12/1992 |
| EP | 0 983 963 A2 | 3/2000 |
| EP | 1 106 570 A2 | 6/2001 |
| WO | WO 00/09441 A2 | 2/2000 |
| WO | WO 03/051771 A1 | 6/2003 |

OTHER PUBLICATIONS

C. Higman et al., "Synthesis Gas Processes for Synfuels Production", EUROGAS '90 Proceedings from the European Applied Research Conference on Natural Gas, Trondheim, Norway May 28-30, 1990, pp. 59-71.
R. Murdoch et al., "Elimination of Carbon Formation in Secondary Reformer System", Ammonia Technical Manual 1996, pp. 82-93.

*Primary Examiner* — Jafar Parsa
(74) *Attorney, Agent, or Firm* — Dickstein Shapiro LLP

(57) ABSTRACT

A process and plant for the production of synthesis gas by a series arrangement of heat exchange reforming and autothermal reforming stages, in which the heat required for the reforming reactions in the heat exchange reforming stage is provided by hot effluent synthesis gas from the autothermal reforming stage. The invention optimizes the operation and control of an arrangement of heat exchange reforming and autothermal reforming stages and involves the introduction of an additional waste heat boiler.

19 Claims, 5 Drawing Sheets

PROCESS FOR REFORMING HYDROCARBONS

FIELD OF THE INVENTION

The present invention relates to a process and plant for production of gas rich in hydrogen and carbon monoxide, particularly synthesis gas for the production of ammonia, methanol, dimethyl ether (DME), hydrogen and hydrocarbons by Fischer-Tropsch (FT) synthesis. The invention relates further to the production of synthesis gas by means of particularly a series arrangement of heat exchange reforming and autothermal reforming stages, in which the heat required for the reforming reactions in the heat exchange reforming stage is provided by hot effluent synthesis gas from the autothermal reforming stage. More particularly, the invention relates to optimisation of the operation and control of an arrangement, particularly a series arrangement, of heat exchange reforming and autothermal reforming stages and introduction of an additional waste heat boiler.

BACKGROUND OF THE INVENTION

The use of a product stream of reformed gas as a source of heat in heat exchange reforming is known in the art. Thus, EP-A-0033128 and EP-A-0334540 deal with parallel arrangements, in which a hydrocarbon feed is introduced in parallel to a tubular reformer and heat exchange reformer. The partially reformed gas from the tubular reformer is then used as heat source for the reforming reactions in the heat exchange reformer.

Other parallel arrangements combine heat exchange reforming and autothermal reforming. EP-A-0983963, EP-A-1106570 and EP-A-0504471 deal with processes in which a hydrocarbon feed is introduced in parallel to a heat exchange reformer and autothermal reformer. The hot product synthesis gas from the autothermal reformer is used as heat exchanging medium for the reforming reactions occurring in the heat exchange reformer.

EP-A-0440258 discloses a process in which the hydrocarbon feed is first passed through a first heat exchange reformer to provide a partially reformed stream. The partially reformed stream is then introduced in parallel to a tubular reformer and second heat exchange reformer. The product streams from both reformers are combined and introduced to an autothermal reformer. The product gas from the autothermal reformer is used as heat source in the second heat exchange reformer, while the product gas from said second heat exchange reformer is used as heat source in the first heat exchange reformer.

Series arrangements are also known in the art. U.S. Pat. No. 4,824,658 and U.S. Pat. No. 6,296,679 (FIG. 2 in both references) disclose a process in which the entire hydrocarbon feed is first introduced to a heat exchange reformer, then passed to a tubular reformer and finally to an autothermal reformer. The product gas from the autothermal reformer is used as heat source in the heat exchange reformer.

U.S. Pat. No. 4,376,717 and our US 2009/0184293 disclose a process in which a hydrocarbon feed is first passed through a tubular reformer; the partially reformed gas is then subjected to heat exchange reforming and finally autothermal reforming. The product gas from the latter is used as heat source in the heat exchange reforming.

Our patent DK 148882 discloses a process for production of synthesis gas, in which the hydrocarbon feed is passed through a heat exchange reforming and autothermal reformer, and where the product gas from the latter is used as heat source in the heat exchange reformer.

The use of heat exchange reformers in the production of synthetic fuels by the Fischer-Tropsch synthesis has significant benefits. Potential benefits compared to other technologies include reduced oxygen consumption, lower capital cost per unit of product, and a higher carbon and energy efficiency. In plants for production of chemicals such as methanol, the use of heat exchange reformers has similar advantages.

In our co-pending patent application PCT/EP2011/006179 we disclose a process in which a hydrocarbon feed is passed through a heat exchange reformer and an autothermal reformer and where the product flow from the latter is used as heat source in the heat exchange reformer. Tail gas from the FT-synthesis is added after the heat exchange reformer and before the autothermal reformer. The addition of tail gas is adjusted to give the desired stoichiometric ratio of $H_2/CO$ equal to about 2 in the effluent stream from the autothermal reformer. Steam is added downstream the autothermal reformer to reduce the aggressivity of the gas passed to the heat exchange reformer with respect to metal dusting.

A specific embodiment also disclosed in PCT/EP2011/006179 is where part of the hydrocarbon feedstock bypasses the heat exchange reformer and is directed directly to the autothermal reformer. This reduces the efficiency of the total plant and increases the oxygen consumption compared to the embodiment without bypass.

It is generally preferred to direct all the product flow from the autothermal reformer to the heat exchange reformer. If only part of the flow is used as heating medium, the size of the heat exchange reformer must be increased to compensate for a lower driving force (lower temperature difference) for heat transfer.

Heat exchange reformers may also be coupled in a similar manner with other partial oxidation reactors. In addition to autothermal reforming (ATR), such reactors include non catalytic partial oxidation (POX) such as gasifiers, and catalytic partial oxidation (CPO), although autothermal reforming (ATR) is preferred. ATR and CPO are provided with a fixed bed of catalyst. As used herein the term autothermal reforming (ATR) encompasses also secondary reforming.

However, for many processes such as those mentioned above, especially for large scale plants comprising a heat exchange reformer and an autothermal reformer, it may be preferred to operate with a low steam-to-carbon ratio. This is for example the case when the produced synthesis gas is to be used for subsequent hydrocarbon synthesis via the Fischer-Tropsch (FT) synthesis. Operation at high steam-to-carbon ratios means higher flow rates due to the increased amount of steam in the feed. In other words, operating at high steam-to-carbon ratios means that the capital cost due to the use of larger equipment may be prohibitively large, especially for large scale plants. Furthermore, high steam-to-carbon ratio means that a larger amount of carbon dioxide is formed in the process. This is in many cases a disadvantage such as for example in plants for the production of synthetic fuels by the low temperature Fischer-Tropsch synthesis. In the low temperature Fischer-Tropsch synthesis carbon dioxide is considered an inert and not a reactant.

Operating at low steam-to-carbon ratios in plants comprising a heat exchange reformer creates a number of challenges. One such challenge is the risk of carbon formation on the catalyst in the heat exchange reformer:

$$CH_4 \rightarrow C + 2H_2 \qquad (1)$$

Carbon on the catalyst may also be formed from higher hydrocarbons (hydrocarbons with two or more carbon atoms in the molecule) or from carbon monoxide according to similar reactions as described in the literature.

The formed carbon may lead to catalyst deactivation and/or catalyst disintegration and build up of pressure drop. This is undesired.

The risk of carbon formation is linked to the catalyst temperature and the steam-to-carbon ratio. For a given feed gas composition and pressure, the steam-to-carbon ratio in the feed gas must be raised if the catalyst temperature is increased. As a higher steam-to-carbon ratio may be uneconomical as described above, it is important to be able to control the temperature in the catalyst of the heat exchange reformer to avoid addition of excessive steam. The temperature control thereby enables operation closer to the carbon limit without exceeding it. In most cases the catalyst temperature reaches its maximum at the outlet of the heat exchange reformer.

Another challenge for the use of heat exchange reformers is metal dusting corrosion. In many cases especially at low steam-to-carbon ratios the prevention or minimisation of metal dusting requires the use of high alloy and/or special materials in the reactor itself. Such alloys are generally expensive and it is therefore generally desired to minimise the size and the heat transfer surface of the heat exchange reformer reactor itself.

In the aforementioned processes comprising a heat exchange reformer upstream and in series with an autothermal reformer, the simultaneous control of the catalyst exit temperature from the heat exchange reformer and the synthesis gas production and quality (e.g obtaining the desired $H_2/CO$-ratio of about 2 for production of synthesis gas for the FT-synthesis) is not straightforward. This is particularly the case when it is considered that the synthesis gas production unit is required to operate under different conditions such as part load and with different natural gas feed and tail gas compositions. Furthermore, the plant production should remain unaffected even in the case of progressive fouling of the heat exchange reformer itself. Fouling is known to the industry and in the art and has in this case the consequence that the heat transferred from the effluent of the autothermal reformer to the catalyst side of the heat exchange reformer is reduced.

In several of the processes described above, the hydrocarbon feed is passed through a heat exchange reformer and then an autothermal reformer and where the product flow from the latter is used as heat source in the heat exchange reformer.

Fouling is known to the person skilled in the art as unwanted material accumulating on the surface of the heat exchanging equipment. This material creates extra resistance to the heat exchange. In a heat exchange reformer the consequence will be that the heat transferred from the effluent of the autothermal reformer to the catalyst side of the heat exchange reformer is reduced.

In the initial period of operation, fouling is generally very low. However, over time, fouling of the heat exchange reformer surface may take place reducing the heat transferred from the autothermal reformer effluent stream to the catalyst side of the heat exchange reformer. This means the exit temperature from the catalyst side of the heat exchange reformer will drop if no countermeasures are taken. The autothermal reformer exit temperature will as a consequence of the lower heat exchange reformer exit temperature also decrease, which again will lead to an additional drop in the heat exchange reformer outlet temperature and so forth. This feed and effluent relationship between the autothermal reformer and heat exchange reformer means that the effect of fouling is amplified, thus a small decrease in the heat exchange reformer ability to transfer heat may lead to a large decrease in heat exchange reformer exit temperature.

This will in turn lead to reduced plant efficiency and/or reduced production, and/or increased oxygen consumption per unit of synthesis gas produced.

In order to maintain conversion of the hydrocarbon feedstock and maintain production, various countermeasures may be considered. The first is to preheat the feedstock to the heat exchange reformer to a higher temperature. However, this requires import of additional fuel and reduces the overall plant energy efficiency. Another alternative is to accept the lower exit temperature (and thereby the lower conversion of the hydrocarbon feedstock) from the heat exchange reformer and increase the conversion in the autothermal reformer. However, this requires additional oxygen and thereby increases the capital cost associated with the expensive air separation unit used to produce the oxygen. In addition, the plant efficiency will normally drop.

An alternative would be to design the size of the heat exchange reformer to take into account the reduction of the heat transfer due to fouling. However, in this case the temperature at the outlet of the heat exchange reformer on the catalyst side during the initial period of operation (before any significant fouling has occurred) could become too high increasing the risk of carbon formation on the catalyst.

As described above in one embodiment of the aforementioned patent application PCT/EP2011/006179, part of the hydrocarbon feedstock bypasses the heat exchange reformer and is directed to the autothermal reformer. In such an embodiment, the fraction of the hydrocarbon feedstock bypassing the heat exchange reformer can be used to control the temperature out of the heat exchange reformer. The heat exchange reformer may for example be designed for a specific bypass during start of operation (before fouling has taken place). As fouling occurs the fraction of the flow bypassing the heat exchange reformer can be increased to maintain the catalyst outlet temperature from the heat exchange reformer. Production can be maintained by increasing the hydrocarbon feedstock flow. However, the plant efficiency will also drop in this case.

It is thus the objective of the present invention to provide a process for production of synthesis gas comprising a heat exchange reformer and an autothermal reformer where the exit temperature from the heat exchange reformer and the synthesis gas production can be maintained during operation with no or very limited loss of efficiency and with no or a very limited increase in the oxygen consumption.

SUMMARY OF THE INVENTION

The preferred layout of a plant for production of synthesis gas is a heat exchange reformer upstream and in series with an autothermal reformer, as per FIGS. 1-5.

According to the present invention, a process for the production of synthesis gas from a hydrocarbon feedstock is provided. The method comprises the first step of:
  a. reforming at least a portion of said hydrocarbon feedstock in an endothermic reforming stage in a heat exchange reformer and withdrawing from the heat exchange reformer an effluent stream of primary reformed gas.

By the term "hydrocarbon feedstock" is meant a stream fed to the process which comprises hydrocarbons. In the broadest sense, hydrocarbons are organic compounds comprising hydrogen and carbon. The hydrocarbons may be as simple as e.g. methane $CH_4$, and may comprise more complex molecules. In addition to the hydrocarbons, the hydrocarbon feedstock may comprise water and/or $CO_2$. The process according to the invention may optionally comprise an additional step of adding water and/or $CO_2$ to a hydrocarbons to provide the hydrocarbon feedstock, prior to the reforming step (step a.).

The term "at least a portion" may comprise the entire hydrocarbon feedstock, or simply a portion thereof.

By "indirect heat exchange" is meant that there is no direct contact between the catalyst and the heating medium, and thereby between the flow passing through the catalyst and the heating medium, because these are separated by a metal wall, i.e. the wall of the tube containing the catalyst.

The hydrocarbons (for example desulphurised natural gas) are mixed with steam and/or carbon dioxide and the resultant hydrocarbon feedstock is directed to the catalyst side of the heat exchange reformer. In the heat exchange reformer, the gas is then steam reformed according to the following reactions:

$$CH_4 + H_2O \leftrightarrow CO + 3H_2 \qquad (2)$$

$$CO + H_2O \leftrightarrow CO_2 + H_2 \qquad (3)$$

Reactions similar to reaction (2) may take place for any higher hydrocarbon present in the feedstock. "Higher hydrocarbons" are hydrocarbons with 2 or more carbon atoms in the molecule (e.g. ethane, propane etc). The gas leaving the heat exchange reformer is close to chemical equilibrium for reactions (2) and (3) above. Typically, the exit temperature is 600-850° C., preferably 675-775° C. and more preferably 700-750° C.

Step (b) of the process of the invention involves b. passing the primary reformed gas from the heat exchange reformer through an autothermal reforming stage (ATR), catalytic partial oxidation stage (CPO) or partial oxidation stage (POX), and withdrawing a stream of hot effluent synthesis gas Autothermal reforming is described widely in the art and open literature. Typically, the autothermal reforming reactor comprises a burner, a combustion chamber, and catalyst arranged in a fixed bed all of which are contained in a refractory lined pressure shell. Autothermal reforming is for example described in Chapter 4 in "Studies in Surface Science and Catalysis", Vol. 152 (2004) edited by Andre Steynberg and Mark Dry.

The partially reformed gas leaving the heat exchange reformer is thus passed to the autothermal reformer. In the autothermal reformer, oxidant gas such as a gas containing at least 90 volt oxygen, and in some cases steam is added. Synthesis gas ("syngas") is formed by a combination of steam reforming and partial oxidation in the autothermal reformer.

By the term "oxidant gas" is meant a stream comprising oxygen, preferably more than 75 vol %, more preferably more than 85 vol %; oxygen. Examples of oxidant gas are air, oxygen, mixture of oxygen and steam, and oxygen enriched air.

The gas leaving the ATR is free of oxygen and generally reactions (2) and (3) above are close to chemical equilibrium. The temperature of this hot effluent synthesis gas from the ATR is between 950 and 1100° C., typically between 1000 and 1075° C.

The hot effluent synthesis gas leaving the autothermal reformer comprises carbon monoxide, hydrogen, carbon dioxide, steam, residual methane, and various other components including nitrogen and argon.

The hot effluent synthesis gas from step (b) is then split into at least a first and a second synthesis gas stream, wherein said first synthesis gas stream is used as heating medium in indirect heat exchange in the heat exchange reformer of step (a). Accordingly, the first synthesis gas stream is passed to the non-catalytic side (hereinafter also called "shell side") of the heat exchange reformer. This first synthesis gas stream is cooled by supplying heat to the catalytic side of the heat exchange reformer by indirect heat exchange to produce a cooled first synthesis gas stream. The exit temperature from the shell side of the heat exchange reformer would typically be in the range from 450-800° C.

The second synthesis gas stream is directed to a second heat exchanger in which it is cooled by indirect heat exchange to produce a cooled second synthesis gas stream. Preferably, said second heat exchanger is a Waste Heat Boiler (WHB) for the production of steam.

Preferably, after leaving the heat exchange reformer, the first cooled synthesis gas stream is further cooled in a third heat exchanger to produce a further cooled first synthesis gas stream. Preferably, the third heat exchanger is a Waste Heat Boiler (WHB) for production of steam.

The further cooled first synthesis gas stream may be mixed together with the cooled second synthesis gas stream from the second heat exchanger to provide a raw synthesis gas product stream, as shown in FIGS. 2-5.

This raw synthesis gas product stream obtained from combining the cooled second synthesis gas stream and the further cooled first synthesis gas stream may be further cooled in one or several additional heat exchangers. This cooling may bring the synthesis gas stream below the dew point temperature. Some or all of the water may thus be removed by condensation to produce a final synthesis gas stream which is directed to the synthesis section of the plant.

Alternatively, the first and second synthesis gas streams may be used separately.

In cases where the synthesis gas is required for a Fischer-Tropsch synthesis unit, a tail gas from the Fischer-Tropsch synthesis unit may be added either upstream or downstream the catalytic side of the heat exchange reformer. Preferably, the tail gas is added upstream the autothermal reforming reactor and downstream the catalytic side of the heat exchange reforming reactor, i.e. the tail gas is added to the primary reformed gas (see FIG. 4). The tail gas contains carbon monoxide, carbon dioxide, hydrogen, various hydrocarbons including olefins and paraffins and a range of other components.

The bypass ratio (defined as the ratio of the flow of second synthesis gas stream to the total flow of the hot effluent synthesis gas from the autothermal reformer) is typically between 1% and 30%, preferably between 2% and 20%, most preferably between 2% and 12%.

A plant would typically be designed for a given bypass ratio at the start of operation. As operation proceeds, the exterior surface of the heat exchange reformer tubes may become fouled leading to a lower amount of heat transferred. The actual bypass ratio when the plant is in operation will then be adjusted to reach certain objectives such as a target catalyst exit temperature from the heat exchange reformer. The reduction of the bypass ratio will increase the difference between the temperature of the stream on the shell side and the temperature on the catalyst side of the heat exchange reformer. The higher temperature difference will increase the heat transferred thus compensating for the effect of fouling.

Should the input of hydrocarbon feedstock be reduced, the flow through the heat exchange reformer and autothermal reformer are also reduced. In such a part load situation the heat exchanger reformer may be too big, which in turn can lead to an undesirable increase in the temperature at the catalyst outlet of the heat exchange reformer. In this case, the bypass ratio may be increased to reduce the heat transferred and thereby decreasing the catalyst exit temperature.

The adjustment of the bypass ratio can conveniently be done by appropriate valves located downstream the shell side of the heat exchange reformer (preferably downstream the third heat exchanger) and also downstream the second heat exchanger used to cool the second synthesis gas stream.

An optional third step of the process involves:

c. adding a stream comprising steam to either said hot effluent synthesis gas from step (b) or to said first synthesis gas stream.

The addition of steam reduces the thermodynamic potential for metal dusting corrosion. Preferably, the stream comprising steam consists of more than 99% of steam. For reasons of economy, the steam is preferably added to the first synthesis gas stream. Further details can be gained from co-pending application PCT/EP2011/006179

In one aspect of the invention a small amount of the hydrocarbon feedstock bypasses the heat exchange reformer and is directed to the autothermal reformer. This small amount is in this embodiment less than 25%, preferably less than 10% and most preferably less than 5%.

In another preferred aspect of the invention, the hydrocarbon feedstock is subjected to a step of pre-reforming, preferably adiabatic prereforming before being directed to the heat exchange reformer. In the adiabatic prereformer most or all of the higher hydrocarbons (hydrocarbon compounds with 2 or more carbon atoms) are converted according to the following reactions:

$$C_nH_m + nH_2O \rightarrow (\tfrac{1}{2}m+n)H_2 + nCO \tag{4}$$

$$3H_2 + CO \leftrightarrow CH_4 + H_2O \tag{5}$$

$$CO + H_2O \leftrightarrow H_2 + CO_2 \tag{6}$$

Reactions (5) and (6) are normally close to equilibrium at the outlet of the prereformer.

The process and plant of the invention are also particularly useful during startup of the Fischer-Tropsch synthesis section in a plant for producing hydrocarbons. In this situation no tail gas is available for recycling from the Fischer-Tropsch section as this section is not yet in operation. In a plant based on heat exchange reforming followed by autothermal reforming in series the $H_2/CO$-ratio which can be generated without recycle of tail gas may not be low enough to allow the startup of the Fischer-Tropsch section.

In order to obtain an $H_2/CO$-ratio as low as possible and as required by the Fischer-Tropsch synthesis section, recycle of part or all of the synthesis gas produced by cooling of the hot effluent gas from the autothermal reforming may be carried out. Typically, this recycle is done after most of the water has been removed by condensation as described earlier.

Recycle of the synthesis gas from the ATR during startup will often be done to a point downstream the heat exchange reformer and upstream the ATR. This means that as the recycle increases (to bring down the $H_2/CO$-ratio), the flow to the shell side of the heat exchange reformer also increases. This occurs without a similar increase in the flow to the catalystic side of the heat exchange reformer. In such a situation, the heat exchanger reformer catalyst outlet temperature may become undesirably high, as more flow is added to the shell side, but not to the tube side of the heat exchange reformer, thereby increasing the heat input to the tube side. This may result in carbon formation on the catalyst in the heat exchange reformer as described above. By splitting the hot effluent synthesis gas from the ATR into first and second synthesis gas streams, as per the present invention, gas flow can be diverted from the shell-side of the heat exchange reformer (first synthesis gas stream) to the second synthesis gas stream. This allows a corresponding reduction in the heat input at the shell-side of the heat exchange reformer and will also reduce the $H_2/CO$-ratio of the gas leaving the autothermal reformer. This is an advantage for start-up of the Fischer-Tropsch section.

In yet another aspect, and in the case where the synthesis gas produced is for a Fischer-Tropsch process, the tail gas is subjected to a step of hydrogenation before being directed to the autothermal reformer. In the hydrogenation step, part or all of the unsaturated hydrocarbons such as olefins are converted into paraffins according to the following reaction (given for olefins);

$$C_nH_{2n} + H_2 \leftrightarrow C_nH_{2n+2} \text{(for } n \geq 2\text{)} \tag{7}$$

The hydrogenation of olefins reduces the potential for i.a. carbon laydown.

The division of the hot effluent gas stream leaving the autothermal reformer appears contradictory to optimising the process from a capital cost point of view. The heat exchange reformer itself becomes larger because the flow of the stream on the shell side is reduced. This reduces the difference between the temperature on the shell side and the catalyst side of the heat exchange reformer. This means that to transfer a specified amount of heat, the heat transfer area of the heat exchange reformer must be increased. Furthermore, an additional heat exchanger (preferably a Waste Heat Boiler) is introduced, which adds further cost.

However, we have found that the disadvantages mentioned above are outweighed by the possibility to ensure that the maximum catalyst temperature out of the heat exchange reformer is not exceeded and especially by the improved possibility of maintaining the production and plant efficiency over time independently of fouling, load and different compositions of natural gas and/or tail gas.

The primary reformed gas may be mixed with tail gas from a Fischer-Tropsch synthesis stage or other downstream process for the production of hydrocarbons, such as tail gas (off-gas) from a process for the production of gasoline from methanol and dimethyl ether, as for instance disclosed in our U.S. Pat. No. 4,520,216 and U.S. Pat. No. 4,481,305. The addition of such tail gas to the synthesis gas production section enables that there is sufficient carbon dioxide during the reforming to achieve the desired $H_2/CO$ molar ratio, typically about 2.0 particularly for Fischer-Tropsch synthesis.

As used herein "tail gas" means off-gas from the Fischer-Tropsch synthesis stage for the production of diesel or downstream process for the production of gasoline which is not re-used in said stage.

A separate stream rich in $CO_2$, i.e. with at least 90 vol % $CO_2$ may be added to the primary reformed gas, or upstream the heat exchange reformer. In one aspect, therefore, the process according to the invention comprises mixing the primary reformed gas or the hydrocarbon feedstock with a gas stream comprising at least 90 vol % $CO_2$.

The heat exchange reformer design may be selected from any heat exchanger layout which can transfer heat from the effluent of the autothermal reformer to the process gas. This includes: shell and tube heat exchanger with segmental baffles, double segmental baffles, disc & doughnut baffles, rod baffles, single helix, double helix, expanded metal baffle or any other suitable baffle configuration including no baffles; double-tube reactor with catalyst disposed inside the double tubes, catalyst disposed outside the double tubes, and/or catalyst disposed outside and inside the double tubes.

Suitably, the process of the invention further comprises the step of converting the separated synthesis gas into ammonia synthesis gas, methanol synthesis gas, dimethyl ether (DME) synthesis gas, synthesis gas for production of hydrocarbons by Fischer-Tropsch synthesis, or synthesis gas for the production of hydrogen, and further converting said synthesis gas into the respective product in the form of ammonia, methanol, DME, liquid hydrocarbons, or hydrogen.

In a particular embodiment of the invention, a portion of the hydrocarbon feedstock bypasses the heat exchange reformer to form a by-pass stream. Tail gas is added to this by-pass stream in case the resultant synthesis gas is to be used for the Fischer-Tropsch synthesis or downstream process for the production of gasoline as described above.

A portion of the hydrocarbon feedstock may be added as a by-pass stream to the primary reformed gas to form a combined stream before entering the ATR, CPO or POX. In a particular embodiment, tail gas is added to this by-pass stream and the thereby formed stream is combined with the primary reformed gas in case the resultant synthesis gas is to be used for the Fischer-Tropsch synthesis synthesis or downstream process for the production of gasoline as described above.

During the process, the pressure measured at the outlet of the ATR is suitably between 15-80 bar, preferably between 20-50 bar.

In the process according to the invention, the process steam-to-carbon ratio ($S/C_{process}$) is suitably in the range 0.4-3.0, preferably 0.5-1.2, more preferably 0.50-1.00. In particular, when the synthesis gas is to be used for the Fischer-Tropsch synthesis, the process steam-to-carbon ratio ($S/C_{process}$) is between 0.4 and 1.3, preferably between 0.6 and 1.1.

The process steam-to-carbon ratio, $S/C_{process}$, means the number of moles steam divided by the number of moles of hydrocarbon carbon. The number of moles of steam includes all the steam added to the hydrocarbon feedstock, e.g. natural gas, upstream the heat exchange reformer. The hydrocarbon carbon includes the hydrocarbons present in the feedstock. The $S/C_{process}$ ratio is measured upstream the heat exchange reformer, or upstream the pre-reformer (if present).

Suitably, for a Fischer-Tropsch process, the $H_2/CO$-molar ratio in the stream of cooled synthesis gas in the first synthesis gas stream is in the range of 1.7 to 2.3, preferably in the range 1.9 to 2.1.

In the case of methanol synthesis, the following molar ratio of components of the synthesis gas lies between 1.7 and 2.3, preferably between 1.9 and 2.1:

$$\frac{H_2 - CO_2}{CO + CO_2}$$

In a specific embodiment the process comprising using valves installed immediately downstream said heat exchangers, preferably waste boilers, for the cooling of the first and second synthesis gas stream for control of the bypass ratio.

In a particular embodiment of the invention, two or more heat exchange reformers are operated in parallel. This may provide advantages with respect to the ease of fabrication of vessels with large diameters containing hundreds of reformer tubes and may allow fine control of the process as well as easier maintenance.

In this embodiment,
at least a second portion of said hydrocarbon feedstock is reformed in an endothermic reforming stage in a second heat exchange reformer and second effluent stream of primary reformed gas is withdrawn from said second heat exchange reformer;

said second effluent stream of primary reformed gas is combined with the effluent stream of primary reformed gas obtained from the reforming the first portion of said hydrocarbon feedstock;

the combined primary reformed gases from the heat exchange reformers are passed through an autothermal reforming stage (ATR), catalytic partial oxidation stage (CPO) or partial oxidation stage (POX), and a stream of hot effluent synthesis gas is withdrawn;

the hot effluent synthesis gas from the autothermal reforming stage (ATR), catalytic partial oxidation stage (CPO) or partial oxidation stage (POX), is split into at least a first synthesis gas stream, a second synthesis gas stream and a third synthesis gas stream, As before, the first synthesis gas stream is used as heating medium in indirect heat exchange in the heat exchange reformer of step (a); and said second synthesis gas stream is directed to a second heat exchanger in which it is cooled by indirect heat exchange to produce a cooled second synthesis gas stream. In addition, the third synthesis gas stream is used as heating medium in indirect heat exchange in the second heat exchange reformer.

The invention also provides a plant for the production of synthesis gas from a hydrocarbon feedstock, as illustrated schematically in FIGS. 1-5. The plant comprises an arrangement of:

at least one heat exchange reformer for producing a primary reformed gas by reforming at least a portion of said hydrocarbon feedstock, an autothermal reformer (ATR), or catalytic partial oxidation apparatus (CPO) or a partial oxidation apparatus (POX) for producing said hot effluent synthesis gas from at least a portion of the primary reformed gas from said heat exchange reformer, optionally, means for adding steam to said hot effluent synthesis gas thereby forming said mixture stream, means for splitting the mixture stream/hot effluent synthesis gas into at least a first synthesis gas stream and a second synthesis gas streams, means for supplying the first synthesis gas stream into the shell-side of the heat exchange reformer, and a second heat exchanger through which the second synthesis gas stream is fed.

In a specific embodiment the plant comprises also a first heat exchanger for further cooling of the first synthesis gas after passing through the heat exchange reformer.

In another specific embodiment the plant comprises also valves installed immediately downstream said first and second heat exchanger. Such valves are advantageously used for control of the bypass ratio.

Preferably said first and second heat exchanger is a waste heat boiler.

Suitably, the plant further comprises an adiabatic pre-reformer upstream the heat exchange reformer.

DETAILED DESCRIPTION OF THE PREFERRED EMBODIMENTS

Figure 1:
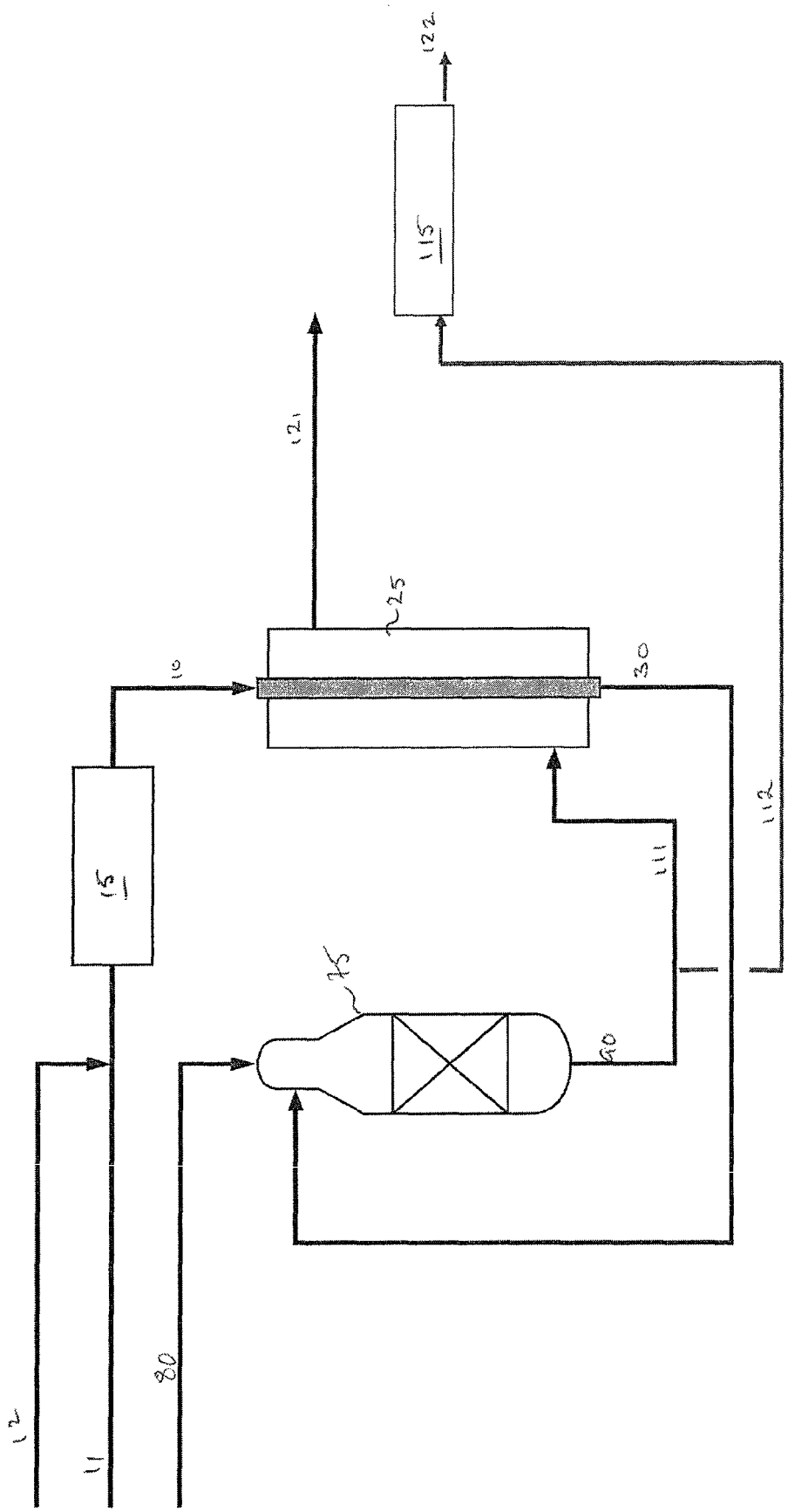
FIG. 1 shows an embodiment of the invention in which the cooled second synthesis gas stream and the cooled first synthesis gas stream are not combined.

In FIG. 1, a hydrocarbon feedstock 10 is formed in a pre-reformer 15 from a hydrocarbon stream 11 and steam 12. The hydrocarbon feedstock 10 is passed to the heat-exchange reformer 25 where it is catalytically steam reformed and thereafter leaves the heat-exchange reformer as stream 30. The primary reformed gas 30 is fed to an autothermal reformer 75 to which oxidant 80 is also supplied. The primary reformed gas is partially combusted and brought towards equilibrium over reforming catalyst in the autothermal reformer 75. The hot effluent synthesis gas 90 from the autothermal reformer 75 is split into first 111 and second 112 synthesis gas streams. Heat is recovered from the first synthesis gas stream 111 by passing it to the heat exchange reformer 25. This first synthesis gas stream 111 is cooled by heat exchange with the gas undergoing reforming over the catalyst in the heat-exchange reformer 25. The thus cooled first synthesis gas stream 111 leaves the heat exchange reformer as stream 121. The second synthesis gas stream 112 is passed through a waste heat boiler 115 to produce a cooled second synthesis gas stream 122 via heat exchange. In the embodiment shown in FIG. 1, the cooled second synthesis gas stream 122 and the cooled first synthesis gas stream 121 are not combined.

Figure 2:
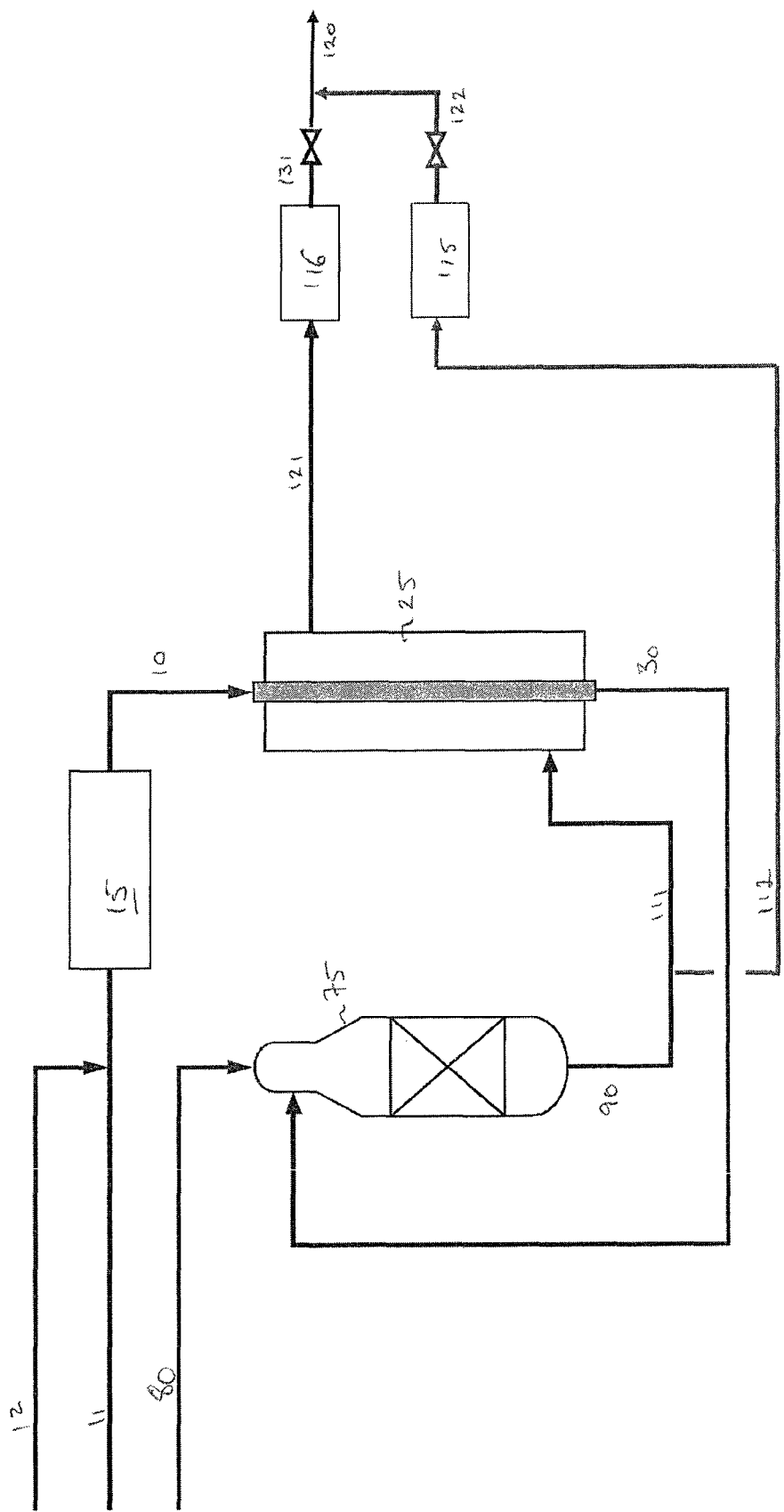
FIG. 2 shows an embodiment of the invention in which the cooled second synthesis gas stream rejoins the further cooled first synthesis gas stream downstream of the heat exchange reformer and a third heat exchanger to form a combined synthesis gas stream.

In FIG. 2, a hydrocarbon feedstock 10 is formed in a pre-reformer 15 from a hydrocarbon stream 11 and steam 12. The hydrocarbon feedstock 10 is passed to the heat-exchange reformer 25 where it is catalytically steam reformed and thereafter leaves the heat-exchange reformer as stream 30. The primary reformed gas stream 30 is fed to an autothermal reformer 75 to which oxidant 80 is also supplied. The primary reformed gas stream 30 is partially combusted and brought towards equilibrium over reforming catalyst in the autothermal reformer 75. The hot effluent synthesis gas 90 from the autothermal reformer 75 is split into first 111 and second 112 synthesis gas streams. Heat is recovered from the first synthesis gas stream 111 by passing it to the heat exchange reformer 25. This first synthesis gas stream 111 is cooled by heat exchange with the gas undergoing reforming over the catalyst in the heat-exchange reformer 25. The thus cooled first synthesis gas stream leaves the heat exchange reformer as stream 121. The cooled first synthesis gas stream 121 is then further cooled in a third heat exchanger 116 (e.g. a waste heat boiler) to provide a further cooled first synthesis gas stream 131. The second synthesis gas stream 112 is passed through a waste heat boiler 115 to produce steam via heat exchange. As shown in FIG. 2, the cooled second synthesis gas stream 122 then rejoins the further cooled first synthesis gas stream 131 downstream of the heat exchange reformer 25 and the third heat exchanger 131 to form a combined synthesis gas stream 120.

Figure 3:
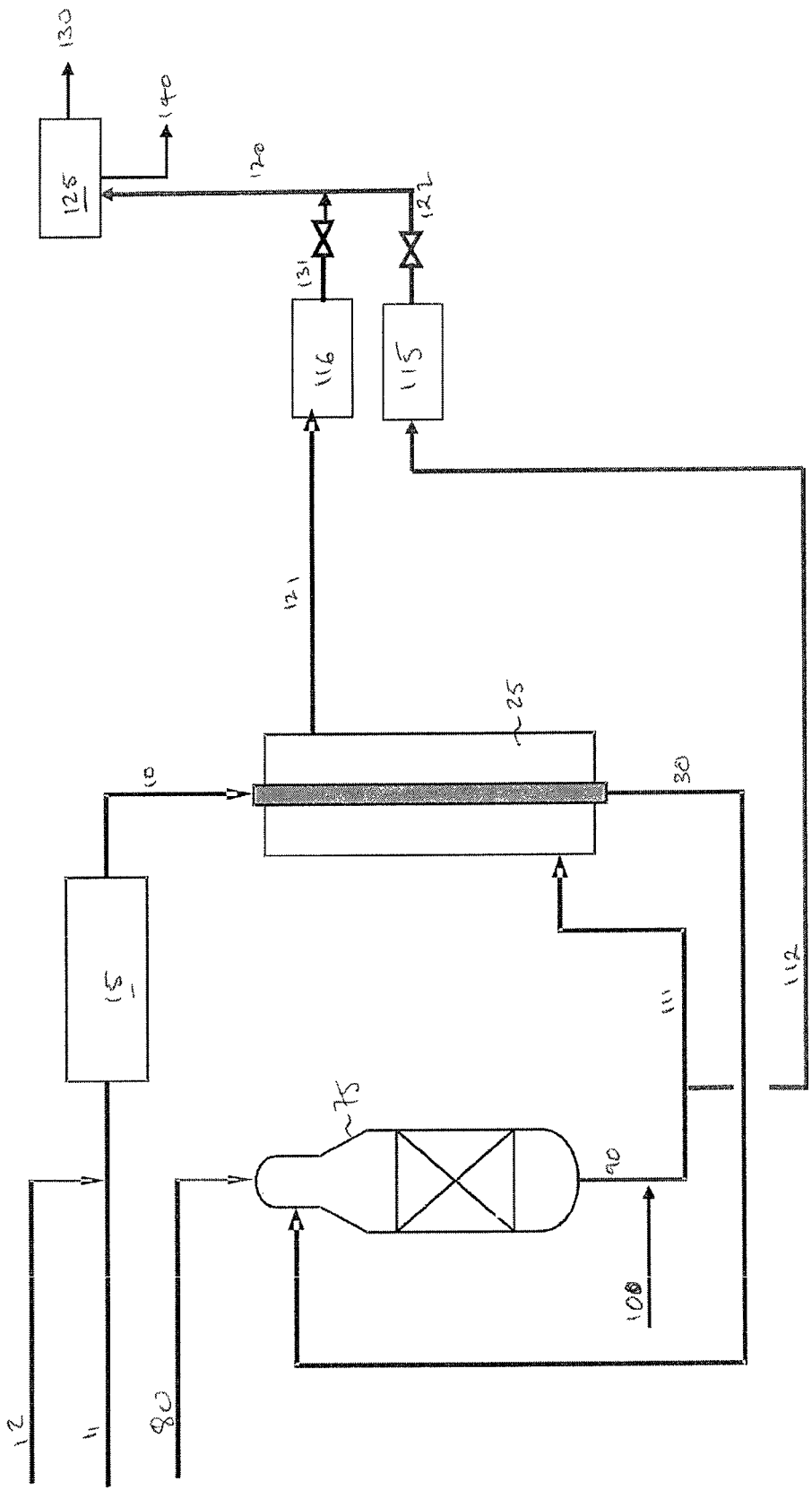
FIG. 3 illustrates a development of the embodiment of FIG. 2 in which the hot effluent synthesis gas from the autothermal reformer is mixed with a $H_2O$ stream to form combined stream prior to being split into first and second synthesis gas streams.

FIG. 3 illustrates a development of the embodiment of FIG. 2. FIG. 3 also shows the step in which the hot effluent synthesis gas 90 from the autothermal reformer 75 is mixed with a $H_2O$ stream 100 to form combined stream 105 prior to being split into first 111 and second 112 synthesis gas streams. In addition, FIG. 3 shows the step in which the combined synthesis gas stream 120 is further cooled in the cooling train and separation units 125 and separated into the product synthesis gas 130 and process condensate 140.

Figure 4:
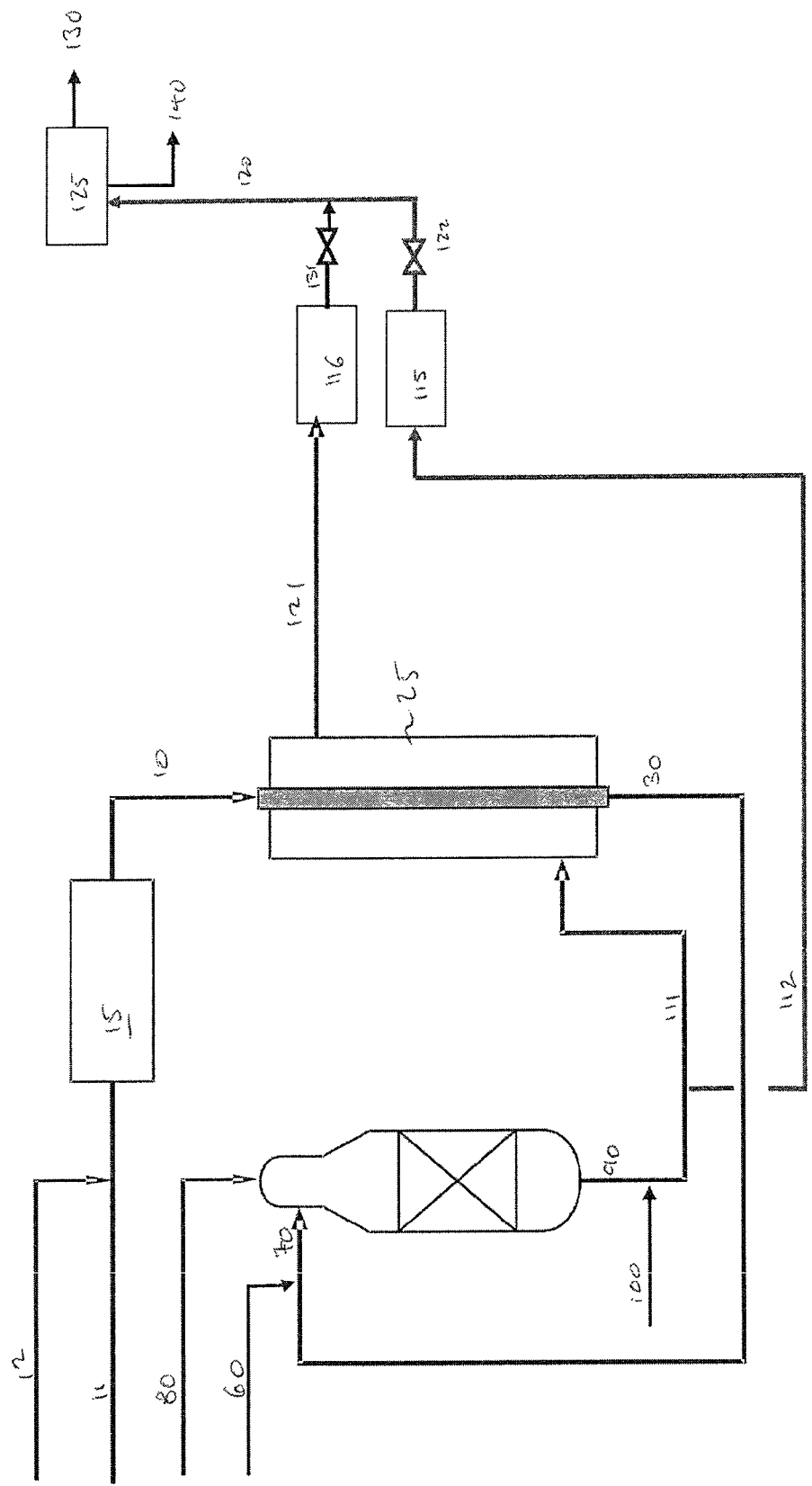
FIG. 4 illustrates a development of the embodiment of FIG. 3, in that the primary reformed gas is mixed with Fischer-Tropsch tail gas forming the ATR feed stream.

FIG. 4 illustrates a development of the embodiment of FIG. 3, in that the primary reformed gas 30 is mixed with Fischer-Tropsch tail gas 60 forming the ATR feed stream 70. The primary reformed gas 30 is mixed with tail gas 60 (containing $CH_4$, higher hydrocarbons, olefins etc.) and other gases ($H_2$, CO, $CO_2$, $N_2$ etc.). This feed stream 70 is fed to the ATR 75 where it is partly combusted and further catalytically reformed to equilibrium. FIG. 4 also shows the optional step in which the hot effluent synthesis gas 90 from the autothermal reformer 75 is mixed with a $H_2O$ stream 100 to form combined stream 105 prior to being split into first 111 and second 112 synthesis gas streams. Finally in FIG. 4, the cooled synthesis gas 120 leaving the heat exchange reformer 25 is further cooled in cooling train and separation units 125 to a low temperature, e.g. 40-80° C., and separated as synthesis gas 130 from the condensate, i.e. water and dissolved gases. The heat may be used for steam and preheating purposes.

Figure 5:
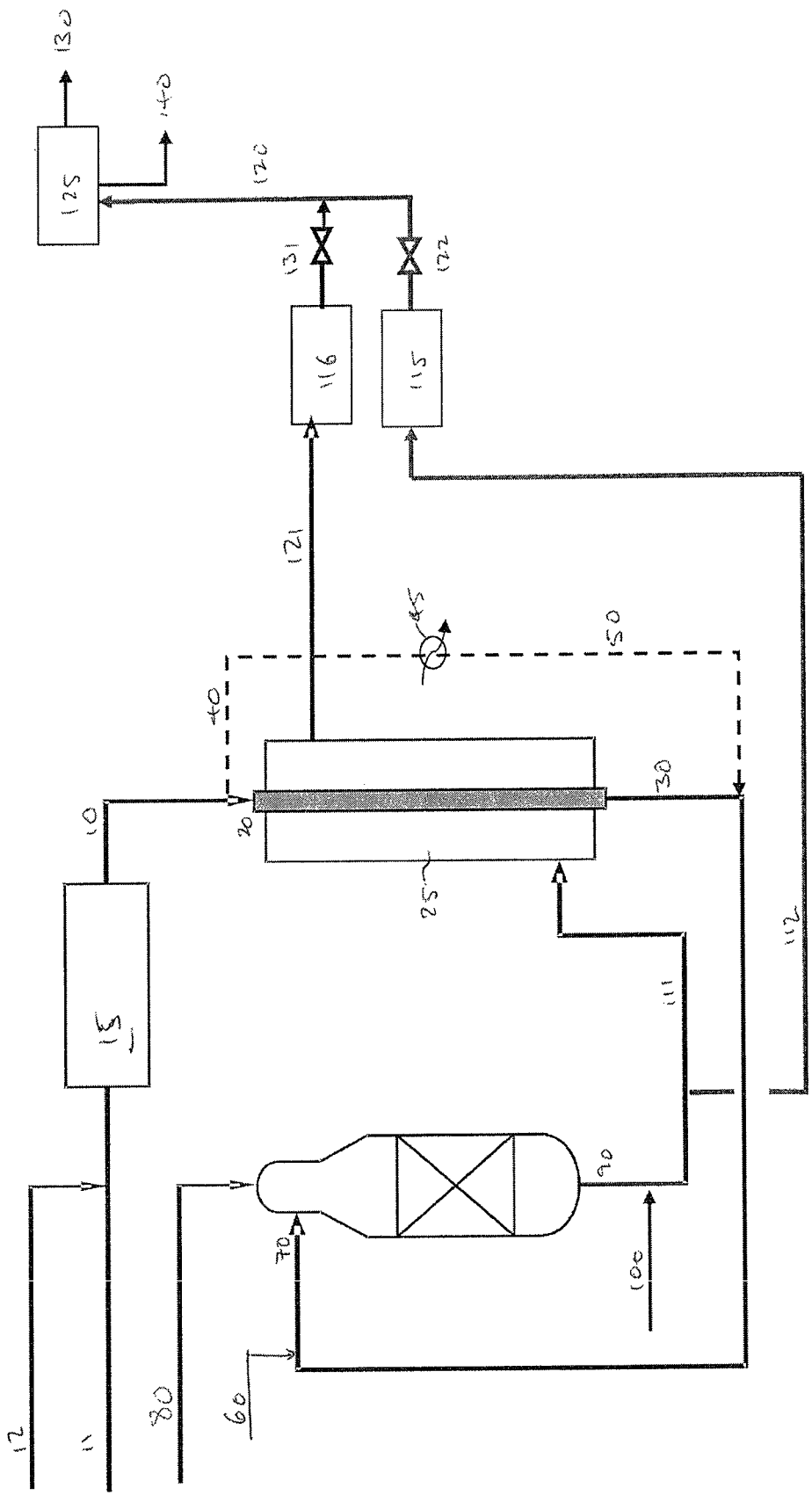
FIG. 5 illustrates an embodiment based on that of FIG. 4. The hydrocarbon feedstock 10 is divided into two streams. The first stream is fed to the heat-exchange reformer where it is catalytically steam reformed and thereafter leaves the heat-exchange reformer as primary reformed gas. The second stream is preheated in a heat exchanger to provide preheated stream. The preheated stream and primary reformed gas are mixed together with Fischer-Tropsch tail gas, forming the ATR feed stream.

The embodiment of FIG. 5 is based on that of FIG. 4. The hydrocarbon feedstock 10 is divided into two streams 20 and 40. The first stream 20 is fed to the heat-exchange reformer 25 where it is catalytically steam reformed and thereafter leaves the heat-exchange reformer as primary reformed gas 30. The second stream 40 is preheated in a heat exchanger 45 to provide preheated stream 50. Preheated stream 50 and primary reformed gas 30 are mixed together with Fischer-Tropsch tail gas 60 forming the ATR feed stream 70. The ATR feed stream is fed to the autothermal reformer 75 to which oxidant 80 is also supplied. The ATR feed stream is partially combusted and brought towards equilibrium over reforming catalyst in the autothermal reformer 75. The hot effluent synthesis gas 90 from the autothermal reformer 75 is split into first 111 and second 112 synthesis gas streams. Heat is recovered from the first synthesis gas stream 111 by passing it to the heat exchange reformer 25. This first synthesis gas stream 111 is cooled by heat exchange with the gas undergoing reforming over the catalyst in the heat-exchange reformer 25. The thus cooled first synthesis gas stream leaves the heat exchange reformer as stream 121. The cooled first synthesis gas stream 121 is then further cooled in a third heat exchanger 116 (e.g. a waste heat boiler) to provide a further cooled first synthesis gas stream 131.

The second synthesis gas stream 112 is passed through a waste heat boiler 115 to produce steam via heat exchange. As shown in FIG. 2, the cooled second synthesis gas stream 122 then rejoins the further cooled first synthesis gas stream 131 downstream of the heat exchange reformer 25 and the third heat exchanger 131 to form a combined synthesis gas stream 120. In addition, FIG. 5 shows the step in which the combined synthesis gas stream 120 is further cooled in the cooling train and separation units 125 and separated into the product synthesis gas 130 and process condensate 140.

In FIGS. 2-5 valves are indicated downstream heat exchangers 115 and 116. It is preferred that one or both of these valves are installed and used for control of the bypass ratio.

In a further aspect, the invention provides a parallel arrangement of heat exchange reformer and autothermal reformer (ATR), catalytic partial oxidation stage (CPO) or partial oxidation stage (POX). As such, a process for the production of synthesis gas from a hydrocarbon feedstock is provided, comprising the steps of:

a. dividing the hydrocarbon feedstock into at least a first and a second hydrocarbon feedstock stream;
 b. reforming said first hydrocarbon feedstock stream in an endothermic reforming stage in one or more heat exchange reformers and withdrawing from the heat exchange reformer an effluent stream of reformed gas;
 c. passing the second hydrocarbon feedstock stream through an autothermal reforming stage (ATR), catalytic partial oxidation stage (CPO) or partial oxidation stage (POX), and withdrawing a stream of hot effluent synthesis gas;

characterised in that the process comprises the step of splitting said hot effluent synthesis gas into at least a first synthesis gas stream and a second synthesis gas stream, wherein said first synthesis gas stream is used as heating medium in indirect heat exchange in the heat exchange reformer of step (b);

and wherein said second synthesis gas stream is directed to a second heat exchanger in which it is cooled by indirect heat exchange to produce a cooled second synthesis gas stream.

In a particular embodiment according to this further aspect of the invention, the first synthesis gas stream may be combined with reformed gas from the heat exchange reformer prior to delivering heat to said heat exchange reformer.

The plant for the production of synthesis gas from a hydrocarbon feedstock in a parallel arrangement, comprises an arrangement of:

means for dividing the hydrocarbon feedstock into at least a first and a second hydrocarbon feedstock stream;
 at least one heat exchange reformer arranged for reforming said first hydrocarbon feedstock stream in an endothermic reforming stage so as to provide an effluent stream of reformed gas;
 an autothermal reforming stage (ATR), catalytic partial oxidation stage (CPO) or partial oxidation stage (POX), arranged for passing the second hydrocarbon feedstock stream through so as to provide a stream of hot effluent synthesis gas;
  optionally, means for adding steam to said hot effluent synthesis gas thereby forming a mixture stream,
  means for splitting the mixture stream/hot effluent synthesis gas into at least a first synthesis gas stream and at least a second synthesis gas stream;
  means for supplying the first synthesis gas stream into the shell-side of the heat exchange reformer, and
  a second heat exchanger through which the second synthesis gas stream is fed.

In a specific embodiment the plant comprises also a first heat exchanger for further cooling of the first synthesis gas after passing through the heat exchange reformer.

In another specific embodiment the plant comprises also valves installed immediately downstream said first and second heat exchanger. Such valves are advantageously used for control of the bypass ratio.

Preferably said first and second heat exchanger is a waste heat boiler.

Suitably, the plant further comprises an adiabatic pre-reformer upstream the heat exchange reformer.

The present invention should not be limited by the above description and enclosed figures. Instead, the skilled person will be able to combine features from various embodiments, while remaining within the scope of the claims. In particular, some embodiments show that steam is added to the hot effluent synthesis gas 90 from the ATR, and that the cooled first 121 and second 122 synthesis gas streams are combined—these steps are optional.

What is claimed is:

1. A process for the production of synthesis gas from a hydrocarbon feedstock, comprising the steps of:
 a. reforming at least a portion of said hydrocarbon feedstock in an endothermic reforming stage in a heat exchange reformer and withdrawing from the heat exchange reformer an effluent stream of primary reformed gas; and
 b. passing the primary reformed gas from the heat exchange reformer through an autothermal reforming stage (ATR), catalytic partial oxidation stage (CPO) or partial oxidation stage (POX), and withdrawing a stream of hot effluent synthesis gas;
 wherein the process further comprises the step of splitting the hot effluent synthesis gas into at least a first synthesis gas stream and a second synthesis gas stream,
 wherein said first synthesis gas stream is used as heating medium in indirect heat exchange in the heat exchange reformer of step (a); and
 wherein said second synthesis gas stream is directed to a second heat exchanger in which it is cooled by indirect heat exchange to produce a cooled second synthesis gas stream.

2. The process according to claim 1, further comprising the step of:
 c. adding a stream comprising steam to either said hot effluent synthesis gas from step (b) or to said first synthesis gas stream.

3. The process according to claim 1 wherein the hydrocarbon feedstock is subjected to a step of pre-reforming before being directed to the heat exchange reformer.

4. The process according to claim 1, wherein the process comprises a further step after the first synthesis gas stream has passed through the heat exchange reformer of: cooling the first synthesis gas stream to a temperature sufficiently low for the steam to condense, and separating the synthesis gas from said condensate.

5. The process according to claim 1, further comprising mixing the primary reformed gas with tail gas from a Fischer-Tropsch synthesis stage or downstream process for the production of gasoline.

6. The process according to claim 1, wherein a bypass ratio, being the ratio of the flow of second synthesis gas stream to the flow of the effluent stream from the autothermal reformer, is between 1% and 30%.

7. The process according to claim 6, wherein, as the process proceeds, the bypass ratio is reduced with time.

8. The process according to claim 1, comprising mixing the primary reformed gas or the hydrocarbon feedstock with a gas stream comprising at least 90 vol % $CO_2$.

9. The process according to claim 1, wherein the heat exchange reformer is selected from a tube and shell heat exchanger, and double-tube reactor with catalyst disposed inside the double tubes, catalyst disposed outside the double tubes, and/or catalyst disposed outside and inside the double tubes.

10. The process according to claim 1, wherein the primary reformed gas from the heat exchange reformer is passed through an autothermal reforming stage (ATR).

11. The process according to claim 1, further comprising the step of converting the separated synthesis gas into ammonia synthesis gas, methanol synthesis gas, dimethyl ether (DME) synthesis gas, synthesis gas for production of hydrocarbons by Fischer-Tropsch synthesis, or synthesis gas for the production of hydrogen, and further converting said synthesis gas into the respective product in the form of ammonia, methanol, DME, liquid hydrocarbons in a downstream process for production of gasoline, or hydrogen.

12. The process according to claim 1, wherein a portion of the hydrocarbon feedstock is led directly as a by-pass stream to the primary reformed gas to form a combined stream before entering the ATR, CPO or POX.

13. The process according to claim 1, wherein the process steam-to-carbon ratio ($S/C_{process}$) is in the range 0.4-3.0.

14. The process according to claim 1, wherein the $H_2/CO$-molar ratio in said stream of cooled synthesis gas in the first synthesis gas stream is in the range of 1.7 to 2.3.

15. The process according to claim 1, wherein, after the heat exchange reformer, the cooled, or further cooled, first synthesis gas stream and the cooled second synthesis gas stream are mixed together to provide a raw synthesis gas product stream.

16. The process according to claim 1, wherein:
at least a second portion of said hydrocarbon feedstock is reformed in an endothermic reforming stage in at least a second heat exchange reformer and an second effluent stream of primary reformed gas is withdrawn from said second heat exchange reformer;
said second effluent stream of primary reformed gas is combined with the effluent stream of primary reformed gas obtained from the reforming the first portion of said hydrocarbon feedstock;
the combined primary reformed gases from the heat exchange reformers are passed through an autothermal reforming stage (ATR), catalytic partial oxidation stage (CPO) or partial oxidation stage (POX), and a stream of hot effluent synthesis gas is withdrawn;
the hot effluent synthesis gas from the autothermal reforming stage (ATR), catalytic partial oxidation stage (CPO) or partial oxidation stage (POX), is split into at least a first synthesis gas stream, a second synthesis gas stream and a third synthesis gas stream, and wherein said first synthesis gas stream is used as heating medium in indirect heat exchange in the heat exchange reformer of step (a);
and wherein said second synthesis gas stream is directed to a second heat exchanger in which it is cooled by indirect heat exchange to produce a cooled second synthesis gas stream;
and wherein said third synthesis gas stream is used as heating medium in indirect heat exchange in the second heat exchange reformer.

17. A process for the production of hydrocarbons or gasoline comprising the step of utilizing the process according to claim 1, during start-up of the Fischer-Tropsch synthesis section in a plant for producing hydrocarbons or downstream process for production of gasoline.

18. A process for the production of synthesis gas from a hydrocarbon feedstock, comprising the steps of:
a. dividing the hydrocarbon feedstock into at least a first and a second hydrocarbon feedstock stream;
b. reforming said first hydrocarbon feedstock stream in an endothermic reforming stage in one or more heat exchange reformers and withdrawing from the heat exchange reformer an effluent stream of reformed gas;
c. passing the second hydrocarbon feedstock stream through an autothermal reforming stage (ATR), catalytic partial oxidation stage (CPO) or partial oxidation stage (POX), and withdrawing a stream of hot effluent synthesis gas;
wherein the process comprises the step of splitting said hot effluent synthesis gas into at least a first synthesis gas stream and a second synthesis gas stream,
wherein said first synthesis gas stream is used as heating medium in indirect heat exchange in the heat exchange reformer of step (b);
and wherein said second synthesis gas stream is directed to a second heat exchanger in which it is cooled by indirect heat exchange to produce a cooled second synthesis gas stream.

19. The process according to claim 18, wherein the first synthesis gas stream is combined with reformed gas from the heat exchange reformer prior to delivering heat to said heat exchange reformer.

* * * * *